(12) United States Patent
Olson

(10) Patent No.: US 9,242,074 B2
(45) Date of Patent: Jan. 26, 2016

(54) MEDICAL DEVICE ANCHOR AND METHOD OF MANUFACTURE THEREOF

(71) Applicant: Medtronic, Inc., Minneapolis, MN (US)

(72) Inventor: Robert L. Olson, Vadnais Heights, MN (US)

(73) Assignee: MEDTRONIC, INC., Minneapolis, MN (US)

(*) Notice: Subject to any disclaimer, the term of this patent is extended or adjusted under 35 U.S.C. 154(b) by 0 days.

(21) Appl. No.: 14/275,656

(22) Filed: May 12, 2014

(65) Prior Publication Data

US 2014/0290029 A1 Oct. 2, 2014

Related U.S. Application Data

(62) Division of application No. 12/545,636, filed on Aug. 21, 2009, now Pat. No. 8,721,598, which is a division of application No. 11/370,741, filed on Mar. 7, 2006, now Pat. No. 7,591,970.

(60) Provisional application No. 60/659,350, filed on Mar. 7, 2005.

(51) Int. Cl.
| | |
|---|---|
| *A61M 25/02* | (2006.01) |
| *A61M 25/00* | (2006.01) |
| *A61M 5/14* | (2006.01) |
| *A61M 5/142* | (2006.01) |
| *A61N 1/05* | (2006.01) |

(52) U.S. Cl.
CPC ............... *A61M 25/02* (2013.01); *A61M 25/00* (2013.01); *A61M 5/1418* (2013.01); *A61M 5/14244* (2013.01); *A61M 5/14276* (2013.01); *A61M 2205/04* (2013.01); *A61N 1/05* (2013.01); *Y10T 29/49826* (2015.01)

(58) Field of Classification Search
CPC . A61M 2205/04; A61M 25/00; A61M 25/02; A61M 5/1418; A61M 5/14244; A61M 5/14276; A61N 1/05; Y10T 29/49826
USPC .......... 264/264, 291, 294–296, 250, 275, 274
See application file for complete search history.

(56) References Cited

U.S. PATENT DOCUMENTS

| | | | | |
|---|---|---|---|---|
| 4,553,961 A | * | 11/1985 | Pohndorf | A61B 17/04 604/175 |
| 4,672,979 A | * | 6/1987 | Pohndorf | A61N 1/375 604/175 |

* cited by examiner

*Primary Examiner* — Imani Hayman
(74) *Attorney, Agent, or Firm* — Withers & Keys, LLC

(57) ABSTRACT

A medical device anchor for use with electrical stimulation leads or catheters, and method of manufacture thereof. The anchor may include a gripping structure and a body portion molded on the gripping structure. The gripping structure forms a serpentine arrangement of a continuous nature with axial segments alternately interconnected between shoulder segments and bridging segments. The shoulder segments extend radially outward relative to the through hole further than the axial segments. The body portion may be formed by molding to securely capture the shoulder in the body portion, with the body portion being molded of material that is softer and more compliant than the gripping structure.

3 Claims, 18 Drawing Sheets

MEDICAL DEVICE ANCHOR AND METHOD OF MANUFACTURE THEREOF

RELATED APPLICATIONS

This application is a divisional application of U.S. Pat. No. 8,721,598, filed on Aug. 21, 2009, which is a divisional application of U.S. Pat. No. 7,591,970, filed on Mar. 7, 2006, which claims priority to provisional U.S. Application Ser. No. 60/659,350, filed Mar. 7, 2005, the entire contents of which are incorporated hereby reference.

FIELD

This application relates to implantable medical leads and catheters, particularly to anchoring devices for use therewith.

BACKGROUND

Medical electrical leads or drug delivery catheters (hereafter referred to as therapy devices) are placed in the contact with biological tissue to delivery a therapy to the patient. These therapy devices are part of a system that may include signal or implantable pulse generators (IPGs) or drug delivery pumps or combinations of such. The stimulators or pumps in the system may be external to, or implanted in, the patient.

Medical electrical leads may be used, for example, to delivery electrical energy to various biological tissues such as the heart, brain, or peripheral nervous system, etc. For example, implantable leads, such as the Medtronic Model 3487A lead, have been used for stimulating the dorsal columns of the spinal cord, or implantable leads, such as the Medtronic Model 3587A, have been used for peripheral nerve stimulation.

Medical drug delivery catheters, for example, may be used to delivery therapeutic agents to the intrathecal space of the spinal canal, or to the blood vasculature, or brain ventricles, etc. Catheters such as the Medtronic Model 8703 may be used for these types of applications.

Retention devices, typically referred to as anchors, are utilized to secure these leads and catheters thereby prevent lead or catheter movement or migrations. U.S. Pat. No. 5,843, 146, which is assigned to Medtronic, discloses a medical lead anchor for anchoring a medical lead relative to, for example, the epidural space of the spinal cord.

Another such anchor is the Medtronic Model 3550 EZ Anchor. This anchor consisted of a molded elastomer, e.g., medical grade silicone rubber, suitable for long-term implantation into a patient. The surface of the Model 3550 EZ Anchor is covered with a pattern of bumps. The bumps allow sutures to be placed in a constricting manner around the midportion of the anchor.

Yet another example is U.S. Pat. No. 4,553,961 (Pohndorf et al), which is entitled "suture sleeve with structure for enhancing pacing lead gripping." One of the embodiments of the suture sleeve of the Pohndorf et al '961 patent includes a gripping enhancing structure, which comprises a framework of an undulating or sinuous, continuous rib including axially extending segments, or simply axial segments, and short partially circular segments, or simply short circular segments. Each short circular segment connects an adjacent pair of axial segments at one end of the framework. Each axial segment of the sinuous rib is spaced an equal distance from each of the adjacent axial segments and this formation purportedly allows for compressibility of framework against a lead body. The short circular segments of the Pohndorf et al '961 patent are shown as being at the same radial distance or position relative to the through-bore of the suture sleeve.

BRIEF SUMMARY OF EXEMPLARY EMBODIMENTS

As used herein, the term, "exemplary" is used in the sense of "for example" or "for purposes of illustration," and not in a limiting sense.

An exemplary medical device anchor is adapted to prevent or resist therapy device migration after the implantation of leads or catheters in a patient. Implantable neurostimulation systems are exemplified in this application for purposes of illustration, but one skilled in the art would realize that the concepts presented would be applicable to other medical devices such as heart pacemaker and defibrillators as well as drug delivery devices and methods.

Exemplary embodiments of the medical device anchor provide: 1) secure lead or catheter retention by compression of beams or linked beams, 2) positive fixation of the gripping element or structure within a soft body of the medical device anchor, 3) unrestricted suture location within a suture zone of the anchor body, 4) soft, flexible tips minimizing or reducing tissue interactions.

A first exemplary embodiment is a medical device anchor that generally comprises a gripping structure and a body portion. The gripping structure has a generally tubular configuration defining axial and radial directions. The gripping structure being defined or formed by an annular shoulder and a plurality of compressible beams extending axially from the annular shoulder wherein the shoulder extends radially outwardly beyond the beams. The body portion is formed by molding around the gripping structure and retains the shoulder within the body portion. The gripping means and body portion define a lumen extending in the axial direction for receiving a lead or catheter.

A second exemplary embodiment is a medical device anchor that generally comprises a gripping structure and a body portion. The gripping structure forms or defines a through hole having a circumference, wherein axial, circumferential and radial directions are defined relative to the through hole. The gripping structure is formed by a plurality of compressible axial segments, a plurality of shoulder segments and a plurality of bridging segments. The plurality of compressible axial segments are arranged in a generally parallel, spaced apart array along the circumference of the through hole, with each axial segment having first and second ends. The plurality of shoulder segments area separated from one another in alternating fashion by a plurality of shoulder gaps forming a generally annular array of shoulder segments and shoulder gaps, with the first ends of the axial segments being alternately bridged or unbridged by the shoulder segments and shoulder gaps. The shoulder segments extend radially outward relative to the through hole further than the axial segments. The plurality of bridging segments are separated from one another in alternating fashion by a plurality of unbridged gaps forming a generally annular array of bridging portions and unbridged gaps, with the second ends of the axial segments being alternately bridged or unbridged by the bridging segments and unbridged gaps such that the gripping structure forms a serpentine arrangement of a continuous nature with the axial segments alternately interconnected between shoulder segments and bridging segments. The body portion is formed by molding to retain the shoulders within the body portion, the gripping structure and body portion defining a lumen for receiving a lead or catheter.

A third exemplary embodiment is a suture sleeve assembly comprising a suture sleeve made of soft elastomeric material and means associated with the suture sleeve for enhancing gripping of a lead body by the suture sleeve. The suture sleeve comprises a tubular sleeve having a throughbore adapted to receive a lead body or catheter. The gripping enhancing means is made of a material that is different than the material of the suture sleeve and which is stiff but flexible, and the gripping enhancing means is positioned to extend within and longitudinally of an elongate axis of the suture sleeve in a suture-receiving area of the suture sleeve intended to receive one or more sutures thereby to disperse any stress placed upon said suture sleeve when sutures are tied along the suture-receiving area. The suture sleeve assembly is radially compressible upon the placement and tying of a suture around the suture sleeve assembly in the suture-receiving area to facilitate generally uniform gripping of the lead body or catheter by the suture sleeve assembly along the length of the gripping enhancing means. The gripping enhancing means comprises a cylindrical flexible framework within a suture sleeve forming a cylindrical envelope. The framework is defined by an undulating or sinuous arrangement of a continuous rib extending in axial segments connected by arcuate segments wherein the arcuate segments define two shoulders extending radially outwardly relative to the through bore farther than the axial segments, and the two shoulders define the suture-receiving area.

A fourth exemplary embodiment is a method of manufacturing the medical device anchor generally comprising forming a gripping structure of the type described above in which the shoulder segments extend radially outward relative to the through hole farther than the axial segments, and molding a body portion on the gripping structure to securely capture the shoulder in the body portion, the body portion being molded of material that is softer and more compliant than the gripping structure.

A fifth exemplary embodiment is a method of manufacturing the medical device anchor generally comprising forming a gripping structure of the type described above in which the shoulder segments extend radially outward relative to the through hole farther than the axial segments, and stretching a body portion on the gripping structure with the shoulder segments securely captured by the body portion, the body portion being molded of material that is softer and more compliant than the gripping structure.

DETAILED DESCRIPTION OF EXEMPLARY EMBODIMENTS

Figure 1:
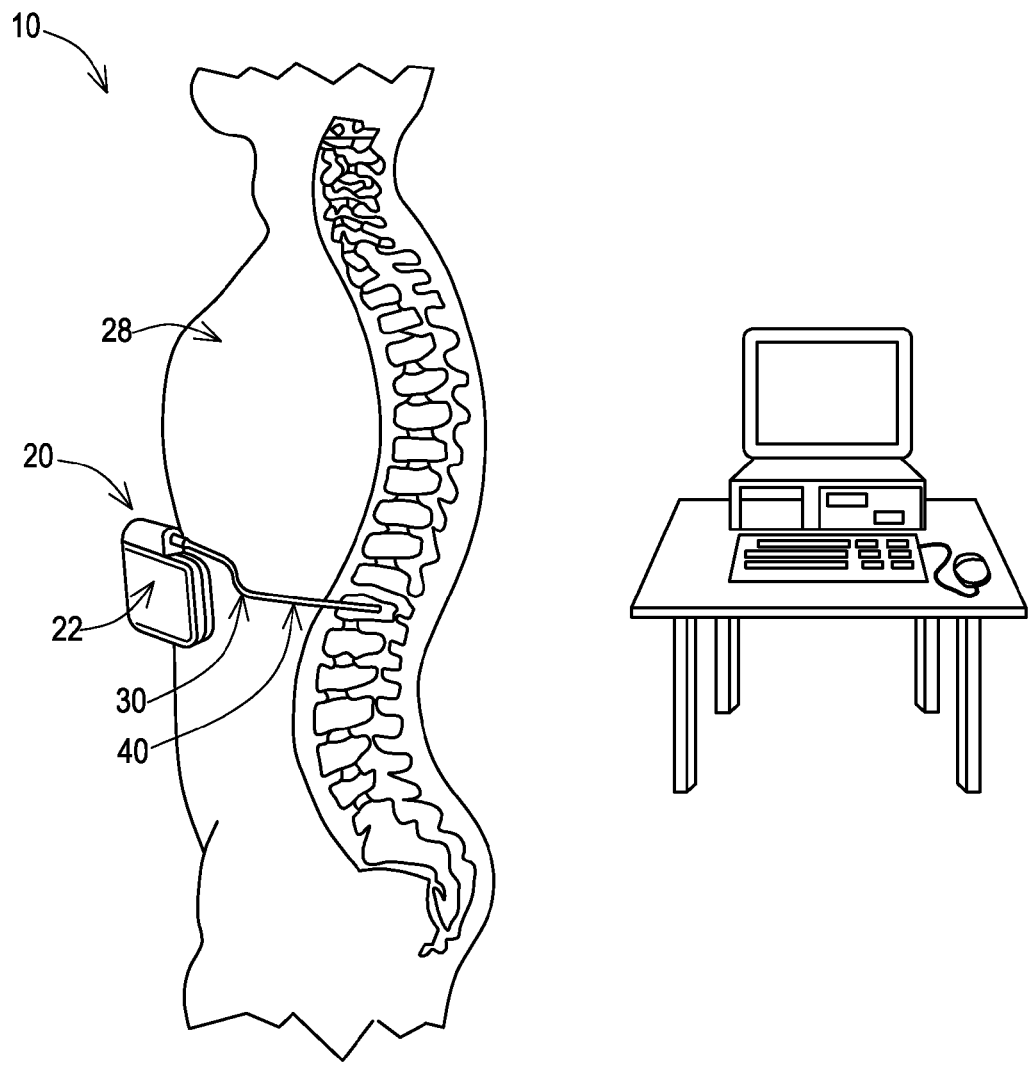
FIG. 1 illustrates an exemplary embodiment of a neurostimulation environment.
Figure 2:
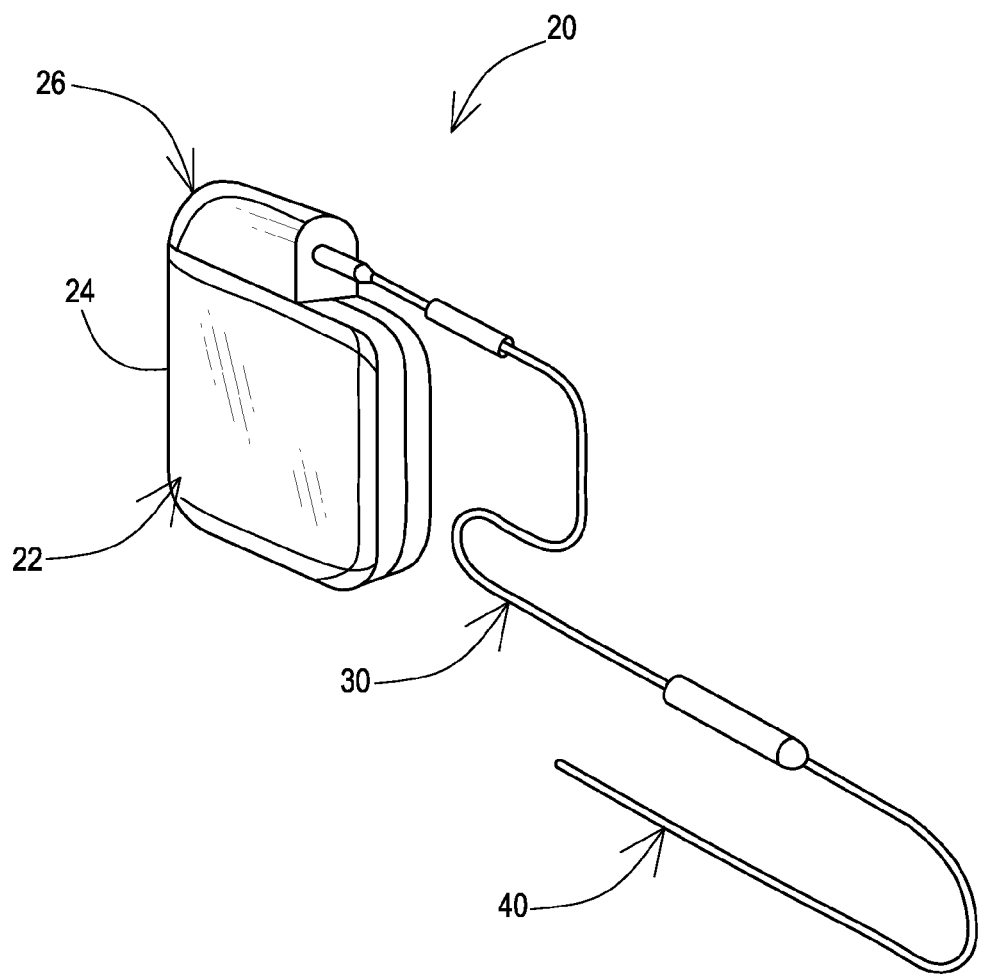
FIG. 2 illustrates an exemplary embodiment of a stimulation system.

FIG. 1 shows a general environmental view 10 for an exemplary implantable neurostimulation system embodiment. Neurostimulation systems may be used to treat conditions such as pain, movement disorders, pelvic floor disorders, gastroparesis, and a wide variety of other medical conditions. As illustrated in FIGS. 1 and 2, the neurostimulation system 20 may include a neurostimulator 22, one or more stimulation lead extension(s) 30, and one or more stimulation lead(s) 40. The neurostimulator 22 is typically implanted subcutaneously in the patient's body 28 at a location selected by the clinician. The stimulation lead 40 is typically fixed in place near the location selected by the clinician using a device such as an adjustable anchor. An exemplary location is within the epidural space for electrical stimulation of the spinal cord, or in or along the brain, or in muscle or subcutaneous tissue.

The exemplary implantable neurostimulator 22 has a housing, a power supply in the housing 24, and stimulation electronics in the housing in electrical communication with the battery and in electrical communication with a connector block 26, which may also be known as a terminal block.

Figure 3:
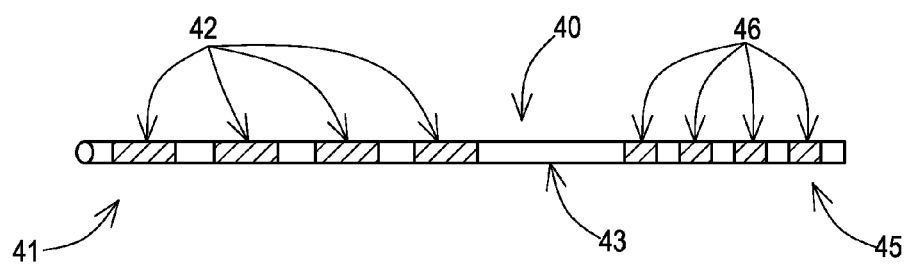
FIG. 3 illustrates an exemplary embodiment of the electrical stimulation lead also shown in FIGS. 1 and 2.

The exemplary stimulation lead 40, shown in FIG. 3, has a proximal end portion 45, a distal end portion 41 and a lead body 43 extending between the proximal end portion 45 and distal end portion 41. The proximal end portion 45 has at least one electrical connector 46 (also known as electrical terminals or contacts), with various standard pluralities, such as four or eight electrical contacts, being typical. The distal end portion 41 has at least one stimulation electrode 42, with various standard pluralities, such as four or eight electrodes, being typical. The exemplary stimulation lead 40 is of the type sometimes referred to as a percutaneous lead, where the lead may have a generally cylindrical configuration throughout its length to facilitate less invasive, percutaneous implantation techniques for totally implanting the lead. Suitable alternatives include surgical or paddle style leads in which an enlarged paddle section is provided on the lead, and the electrodes are typically arranged along the paddle section.

There is at least one lead conductor 49 contained in the lead body 43 that is electrically connecting the electrical connector 46 to the stimulation electrode 42. Typically, at least one conductor may be used to establish electrical communication between a single electrical connector/electrode pair, although alternative examples include multiplexing or bus features within the lead to allow use of fewer conductors along the length of the lead than the number of electrodes. As used herein, "conductive means" or "means for electrical communication between electrodes and electrical connectors include the foregoing examples or any alternative structure to allow selection or electrical activation of one or more electrode.

Figure 4:
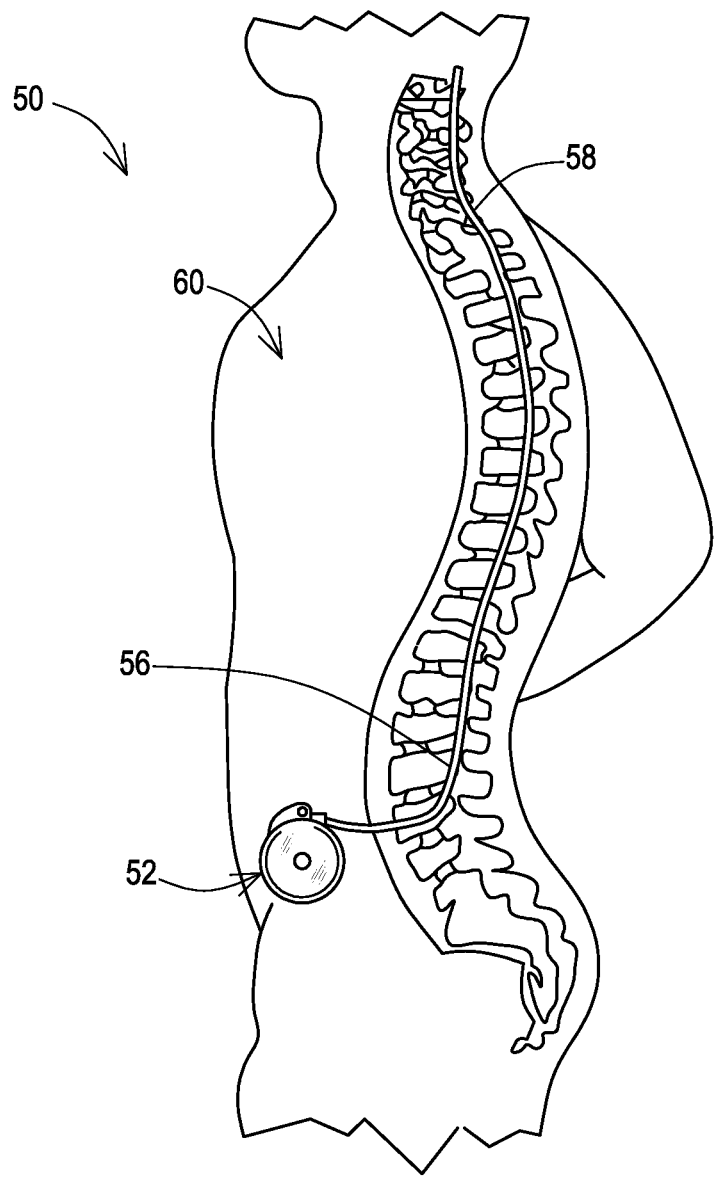
FIG. 4 shows an exemplary embodiment of a drug delivery environment.
Figure 5:
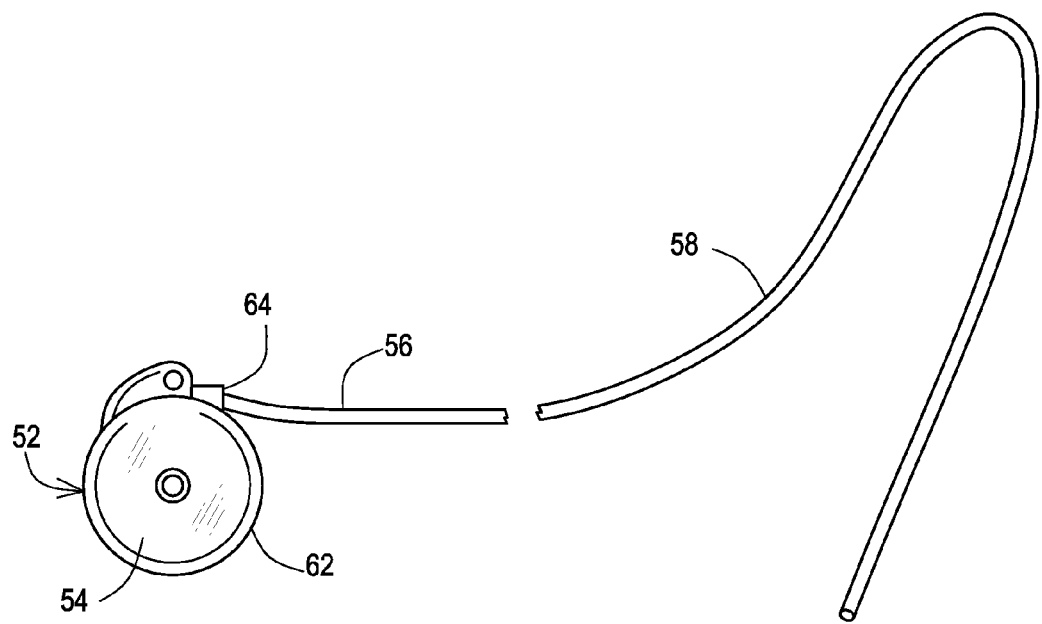
FIG. 5 shows an exemplary embodiment of a drug delivery system.
Figure 6:
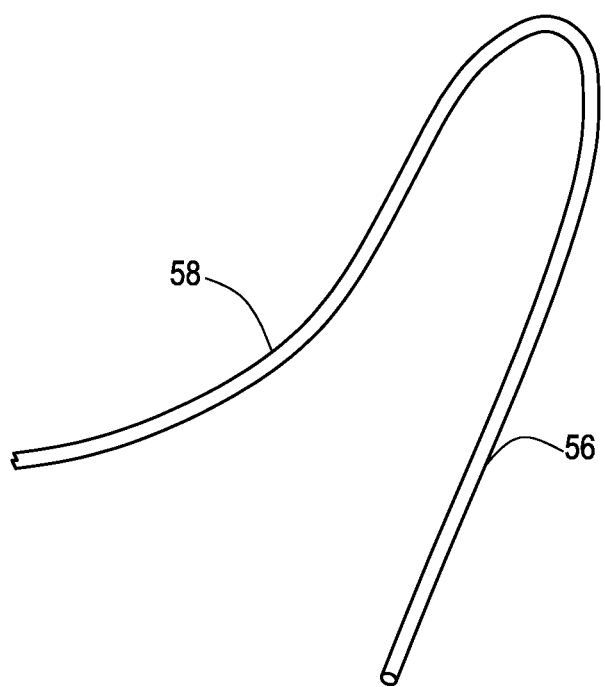
FIG. 6 shows the exemplary embodiment of a catheter of FIGS. 4 and 5.
Figure 7:
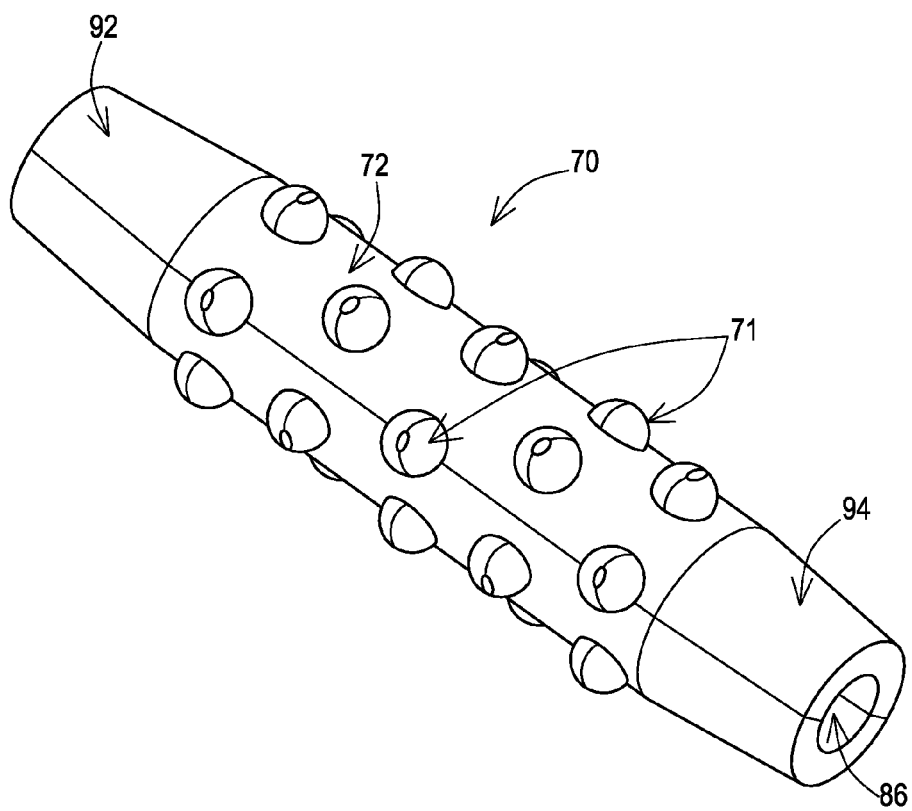
FIG. 7 is a perspective view of preferred exemplary embodiment of a medical device anchor.

FIG. 4 shows a general environmental view 50 for an exemplary embodiment of an implantable drug delivery system 52. Drug delivery systems may be used to treat conditions such as pain, movement disorders, diabetes and a wide variety of other medical conditions. As illustrated in FIGS. 4 and 5, the drug delivery system 52 may include a drug delivery pump 54, and a catheter having a proximal catheter portion 56 and a distal catheter portion 58. The drug pump 54 is typically implanted subcutaneously in the patient's body 60 at a location selected by the clinician. The distal catheter portion 58 is typically fixed in place near the location selected by the clinician using a device such as an adjustable anchor.

The exemplary implantable drug delivery pump 54 may have a housing 62, and a power supply, pumping mechanism and pump electronics in the housing 62. The pumping mechanism may be in direct communication with the catheter through a connector 64 on the housing 62.

The catheter is typically has a tubular configuration with a lumen extending longitudinally throughout the catheter. Implantable catheters may be formed of various medical grade materials, including for example silicone or polyurethane. More that one lumen may alternatively be present in the catheter. The therapy delivery element in a drug delivery system may include a distal catheter and an optional proximal catheter. Elements may be included in proximal catheter to provide hoop strength to the device to prevent kinking or crushing of the proximal catheter.

Figure 8:
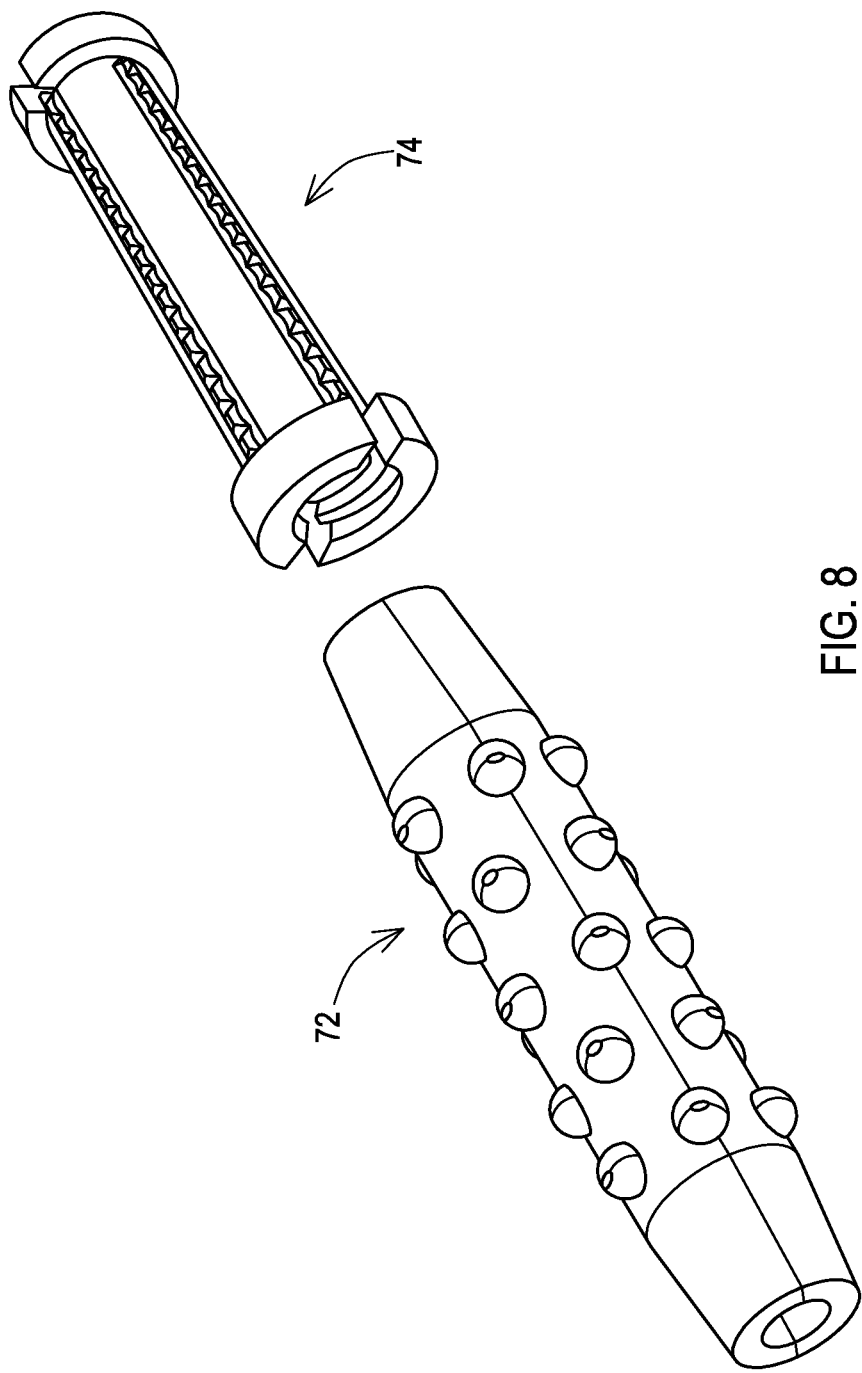
FIG. 8 is an exploded view of the medical device anchor of FIG. 7.

FIGS. 7-11 illustrate an exemplary embodiment of a medical device anchor or suture sleeve 70 having a body portion 72 and gripping element or structure 74, both shown in an exploded view in FIG. 8. The gripping element or structure 74 constitutes an exemplary embodiment of a means associated with the suture sleeve for enhancing gripping of a lead body or catheter by the suture sleeve, or gripping enhancing means.

The gripping structure 74 may be formed of a material having different mechanical properties than the material of the body portion 72. The gripping structure 74 may, for example, be formed of relatively stiff material in comparison with the material of the body portion 72. The body portion 72 may be formed, for example, of soft, resiliently compressible material, such as elastomeric or substantially elastomeric medical grade material (e.g., silicone or polyurethane), including without limitation silicone rubber having a Shore A hardness of approximately 45-55. The gripping structure 74 may be formed, for example, of Titanium or Titanium alloy material.

Figure 9:
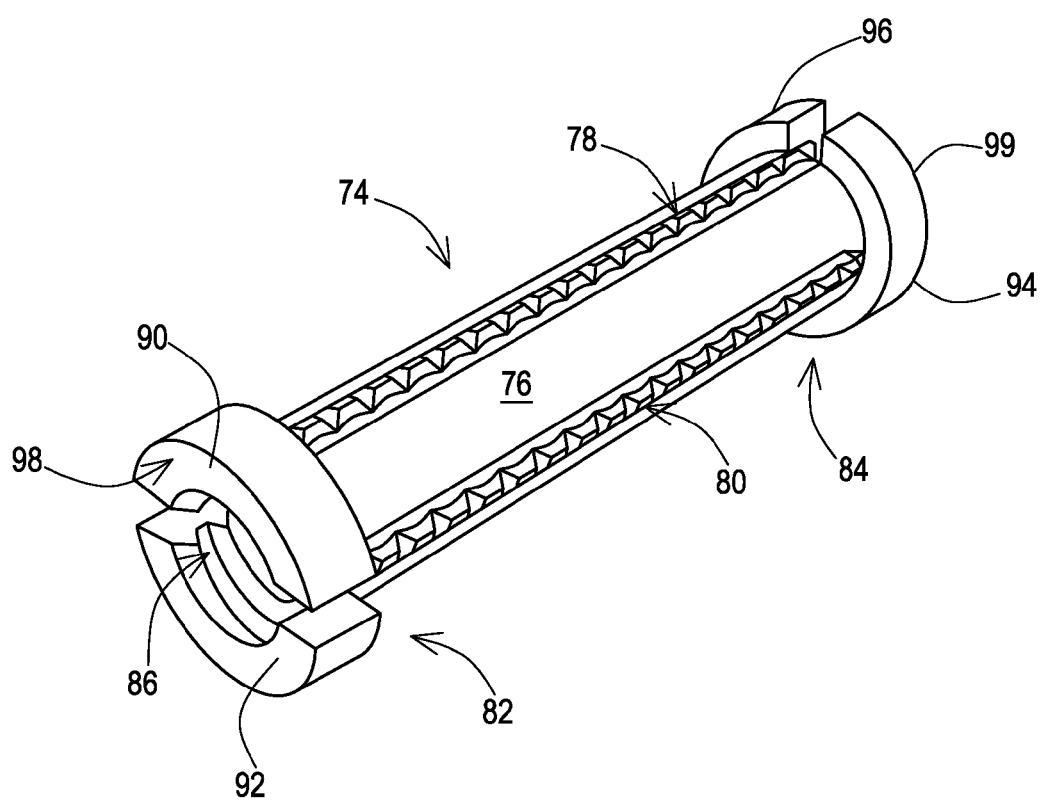
FIG. 9 is a perspective view of an exemplary embodiment of a gripping structure of the medical device anchor of FIGS. 7 and 8.
Figure 10:
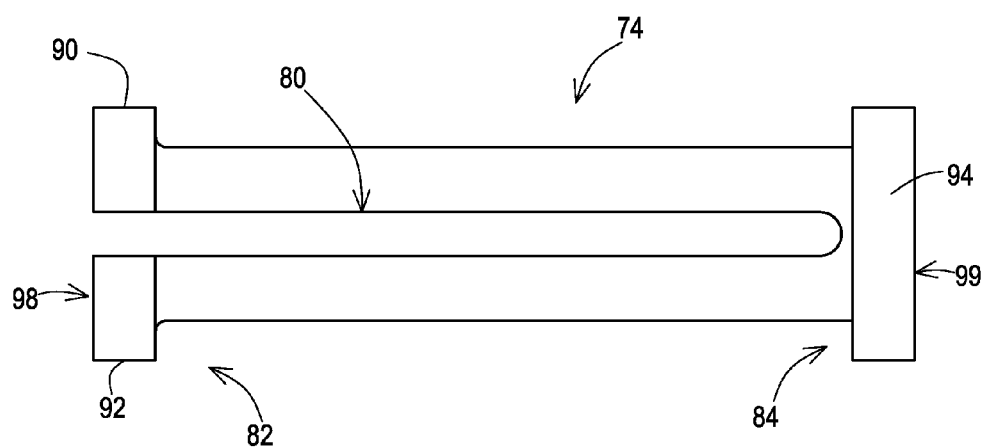
FIG. 10 is a right side view of the gripping structure of FIG. 9.

As illustrated in FIG. 9, the gripping structure 74 may include compressible axial segments or beams 76 separated by slots (e.g., slots 78 and 80), and raised shoulders 82 and 84 at opposite ends of the axial segments 76, with the axial segments and raised shoulders defining a generally cylindrical lumen or through hole 86. Axial, circumferential and radial directions are defined relative to the through hole 86.

In the exemplary embodiments shown in FIGS. 7-11, four axial segments 76 and four shoulder segments 90, 92, 94 and 96 are illustrated, but it will be understood that alternative numbers of such axial segments and shoulder segments may be provided.

The gripping structure 74 may be viewed as a generally cylindrical tubular structure being partially split by a first slot 78 and second slot 80 extending longitudinally from opposite ends 98 and 99 of the gripping section 74, where the first and second slots 78 and 80 define two planes approximately perpendicular to one another. The first slot 78 bisects the cross-section of the gripping structure 74 along a first plane from the first end 98 of the gripping structure 74 up to shoulder 82 (shoulder segments 90 and 92). The second slot 80 bisects the cross-section of the gripping structure 74 along a second plane from the second end 99 up to shoulder 84 (shoulder segments 94 and 96). The first and second planes defined, respectively, by the first and second slots 78 and 80 are approximately perpendicular to one another. Slot 78 form two gaps one along each of first and second opposite sides of the gripping structure, and slot 80 forms two gaps one along each of third and fourth opposite sides of the gripping structure. Slots 78 and 80 (or the gaps formed thereby) allow the gripping section to be compressed by the application of a radial force, such as suture. The gripping structure 74 thus forms a serpentine arrangement of a continuous nature with the axial segments 76 (defined between the slots) alternately interconnected between shoulder segments 90, 92, 94 and 96. As used herein, the terms "plane" or "planes" (e.g., "first plane" or "second plane") are used in a geometric sense to establish relative positions or orientations and such planes do not constitute physical structure but merely are used to define an illustrative relationship between elements, such as the axial segments or first and second slots, that do constitute illustrative or exemplary physical structure.

It will be appreciated that the gripping structure may alternatively include a different number of slots extending from opposite ends in a similar fashion to first and second slots 78 and 80. For example, four slots (not shown) could be provided in which two slots extend inwardly from each end, the slots extending from the same end define planes that are approximately perpendicular to each other, and the slots extending from opposite ends define planes that are offset by approximately 45 degrees from one another.

The plurality of the compressible axial segments 76 may be, for example, arranged in a generally parallel, spaced apart array along the circumference of the through hole 86, with each axial segment having first and second ends. The plurality of shoulder segments 90 and 92 or 94 and 96 of each of shoulders 82 and 84 are separated from one another in alternating fashion by a plurality of shoulder gaps forming, for each shoulder, a generally annular array of shoulder segments and shoulder gaps. The first ends of the axial segments are alternately bridged or unbridged by the shoulder segments 90, 92 and shoulder gaps of first shoulder 82, and the second ends of the axial segments are alternatively bridged or unbridged by the shoulder segments 94, 96 of the second shoulder 84 such that the gripping structure forms a serpentine arrangement of a continuous nature with the axial segments alternately interconnected between shoulder segments 90, 92, 94 and 96.

The shoulder segments 90, 92, 94 and 96 extend radially outward relative to the through hole farther than the axial segments. The axial segment array may be viewed as defining a first infinite cylinder surrounding and tangent with the axial segment array, with the at least one of the shoulder segments (but preferably all of the shoulder segments 90, 92, 94 and 96) being substantially entirely radially outward of the first infinite cylinder. As used herein, the term "infinite cylinder" refers to a geometric concept of a cylinder having an infinite length whose circumferential surface is defined by the axial segment array to facilitate understanding the geometric arrangement or relationship of the shoulders or shoulder segments relative to the axial segment array. The term "infinite cylinder" is not an actual physical structure of such gripping structure.

Figure 15:
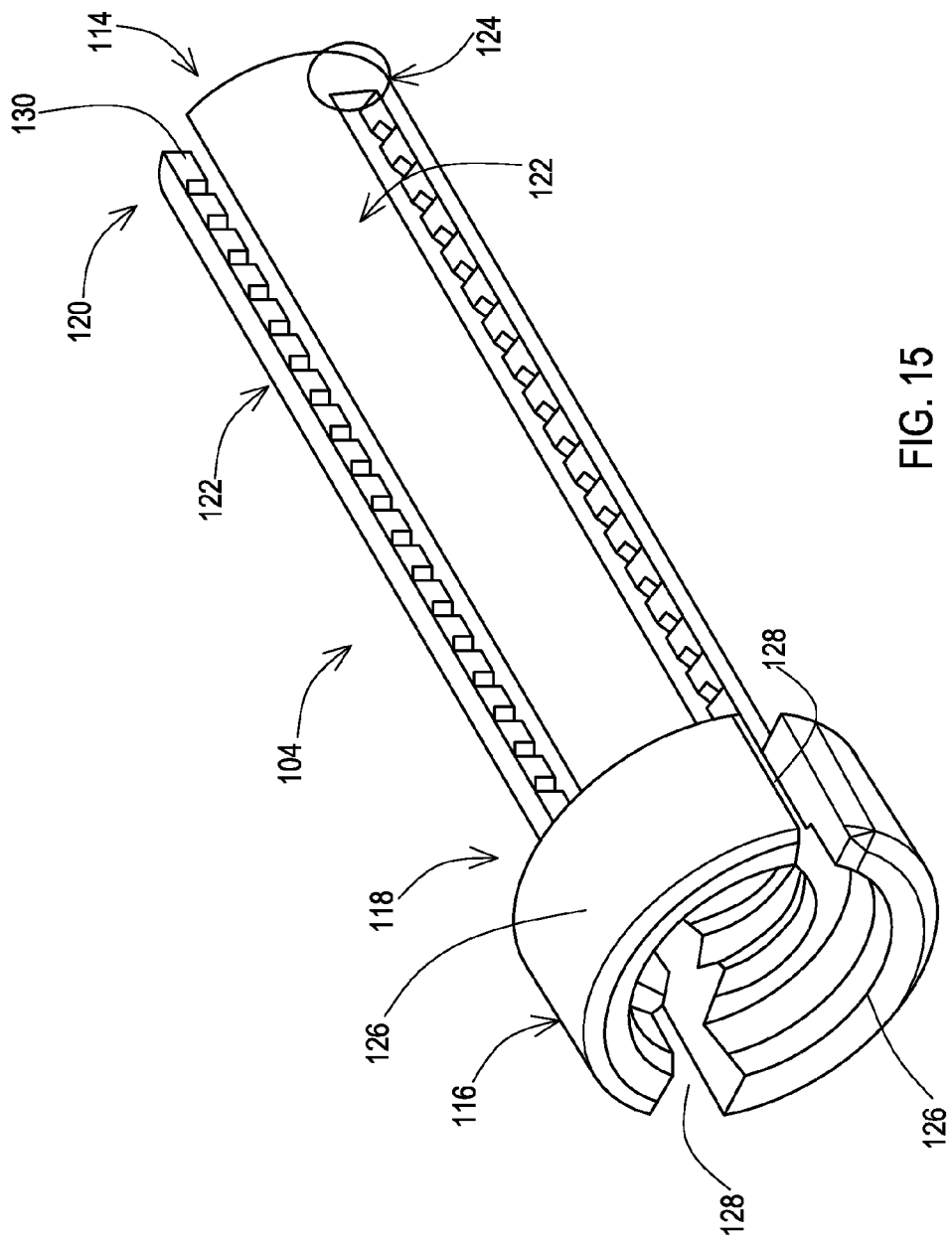
FIG. 15 is a perspective view of an exemplary embodiment of a gripping structure of the medical device anchor of FIGS. 13 and 14.

Most preferably, each of the shoulder segments 90 and 92 include a portion extending axially beyond the first ends of the axial segments, and each of the shoulder segments 94 and 96 include a portion extending axially beyond the second ends of the axial segments. This arrangement is best shown in FIG. 15 with respect to a single shoulder having two shoulder segments in the context of a different embodiment of the medical device anchor. The body portion may then be molded to substantially surround such extended portions of the shoulder or shoulders for particularly effective retention of the gripping structure within the body portion. The extended portions of the shoulders may be viewed as being positioned radially outside the first infinite cylinder.

Figure 11:
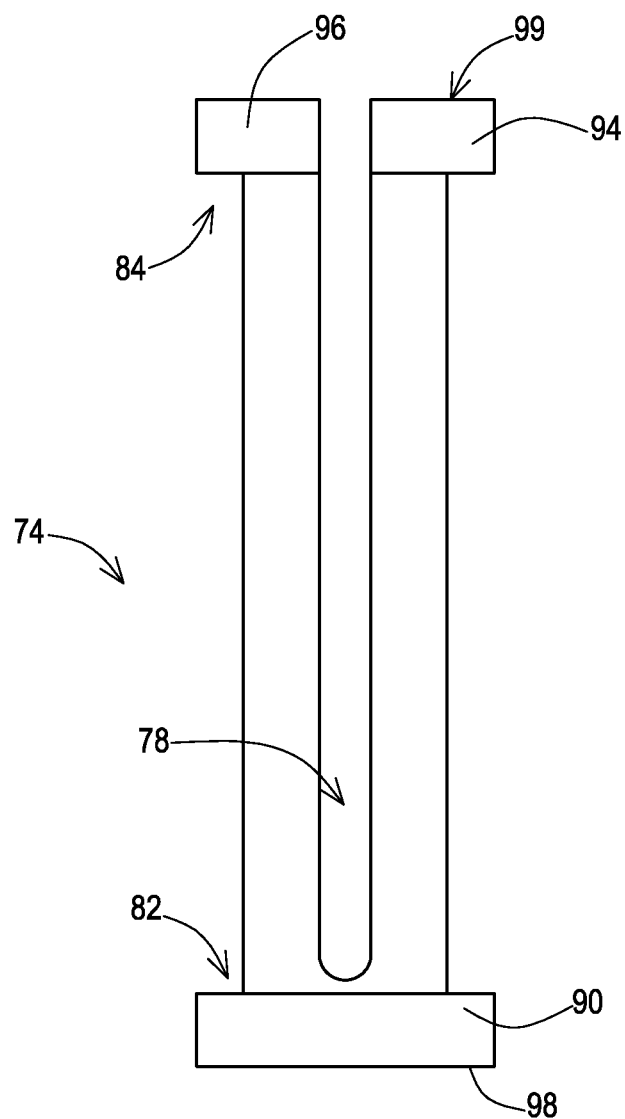
FIG. 11 is a top view of the gripping structure of FIGS. 9 and 10.
Figure 12:
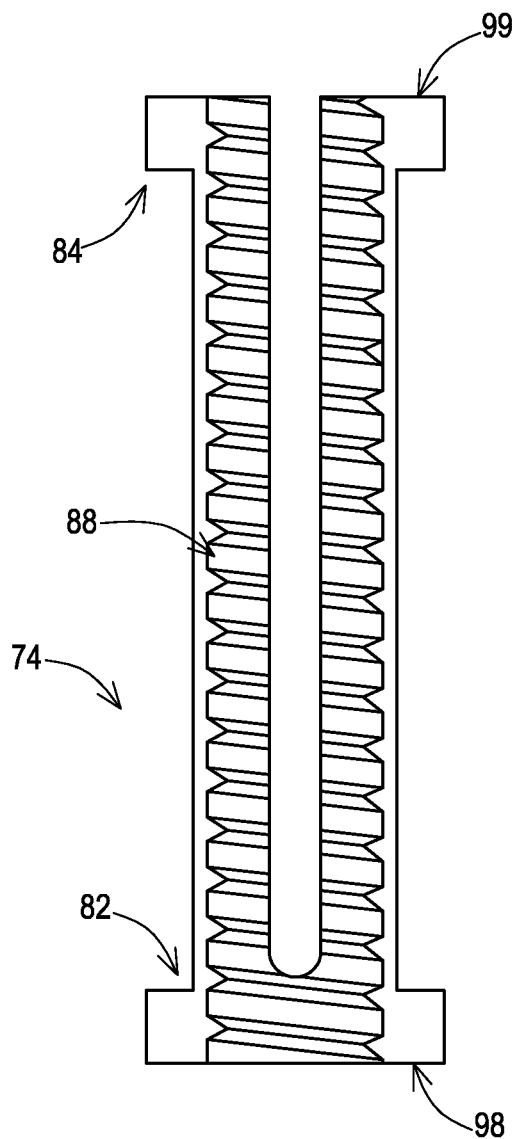
FIG. 12 is a cross-sectional view of the gripping structure of FIGS. 9-11.
Figure 13:
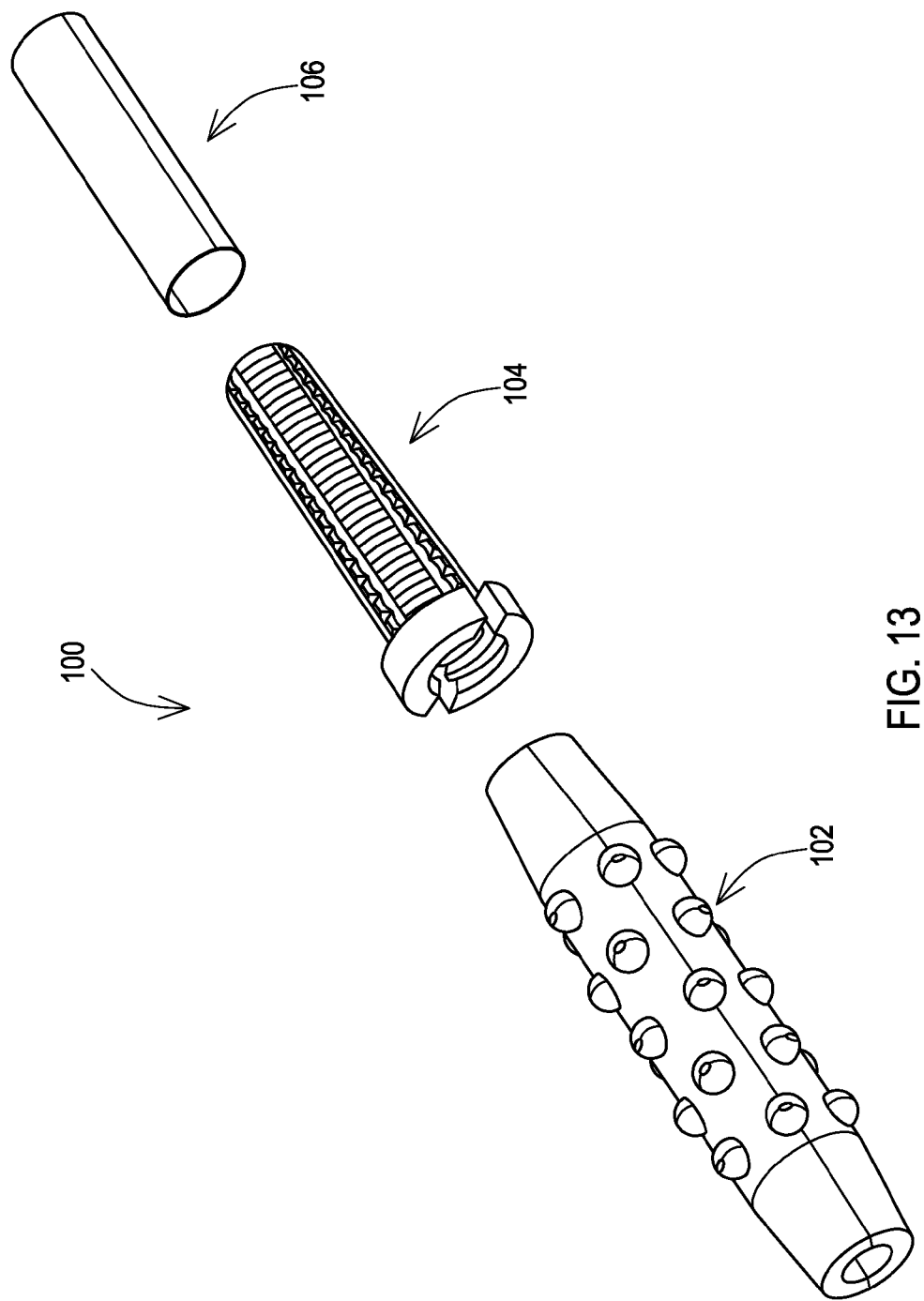
FIG. 13 is an exploded view of an alternate exemplary embodiment of the medical device anchor.

In a preferred example, threads 88 or other suitable texture is provided on the inner surface of the axial segments 76 (and optionally in the shoulders) for retention against a catheter or lead held within the lumen 86. FIG. 11 is a cross-sectional view of gripping structure 74 illustrating an exemplary embodiment of the inner surface of the lumen 86 of gripping structure 86. The inner surface may be intentionally roughened to increase the frictional force to resist lead or catheter withdrawal when a tensile force is applied to the lead or catheter. This roughened surface may take a multitude of forms, with a preferred exemplary form being that of threads 88. Threads 88 are shown in FIG. 11 to completely cover the lumen-defining surfaces, although the lumen-defining surfaces of the axial segments 76 could be roughened, with the inner surfaces of the shoulder segments in at least one example being separated from the lumen by material of the body portion.

Exemplary surface features, such as bumps 71, may be provided along the outer surface of the midportion of the body portion 72, and tapered end portions 92 and 94 may also be provided.

FIGS. 13-17 illustrate an alternate exemplary embodiment of a medical device anchor 100 including a body portion 102, gripping means or gripping structure 104 and sleeve 106. Sleeve 106 substantially enclosing the outer surface of the gripping structure 104 to provide a shield during an exemplary insert molding process. Sleeve portion 106 may be tubing fabricated from a material such as polytetrafluoroethylene, nylon or other materials, but is preferably formed of the same or similar material to that used to mold the body portion (e.g., silicone rubber).

The body portion 102 includes a midportion 108 and tapered endportions 110 and 112. The body portion 102 has a lumen or through hole 114 therethrough defining a longitudinal direction, with the lumen or through hole 114 being adapted to accept a lead or catheter. Body portion 102 is made from biocompatible materials such as silicone rubber, polyurethane or other elastomer.

Midportion 108 has an outer surface on which a pattern of bumps are formed. The illustrative bumps are spheroidal in nature, but could assume other geometric shapes. In practice, a suture or sutures may be place circumferentially around the midportion 108 to apply a constricting force effecting lead or catheter retention. Optionally, the body portion 102 may alternatively or additionally include radial grooves in the outer surface providing suture locations.

Figure 14:
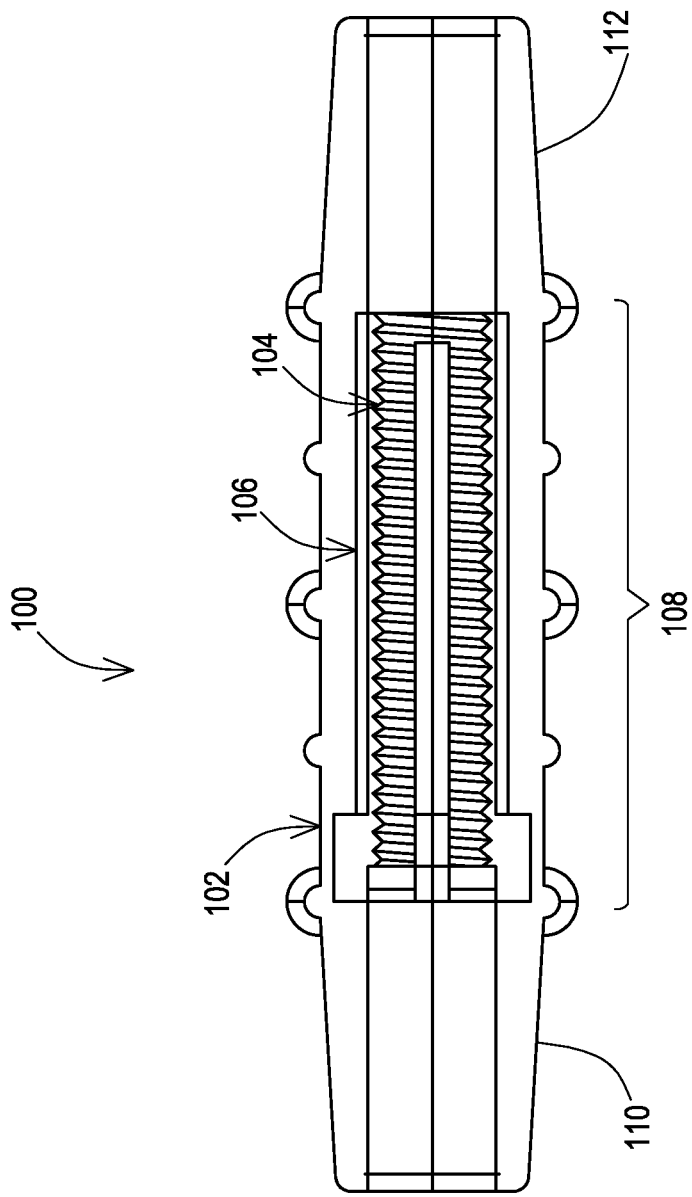
FIG. 14 is a cross-sectional view of the medical device anchor of FIG. 13.

Gripping means 104 and sleeve 106 are shown in situ in the body portion 102 in FIG. 14. The gripping means 104 and sleeve 106 may be positioned such that the tapered endportions 110 and 112 are symmetrically located about the gripping means 104.

Figure 16:
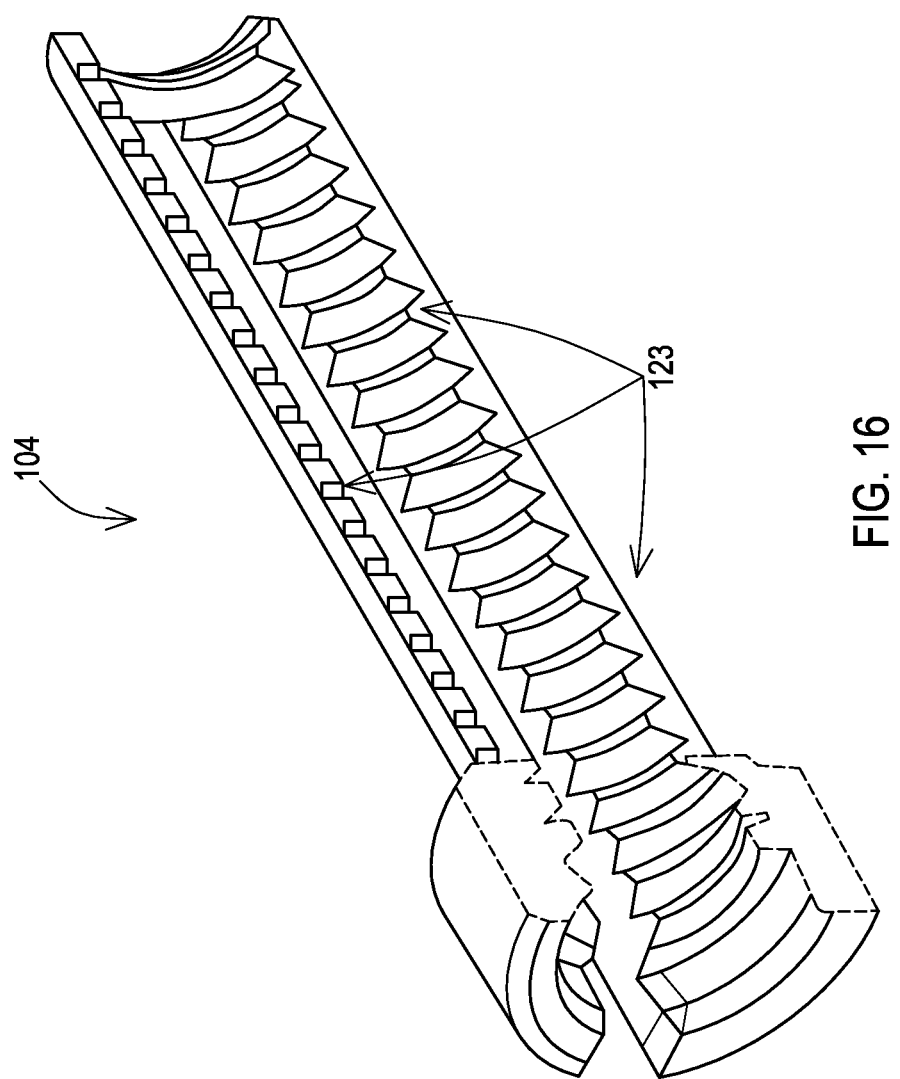
FIG. 16 is a cross-sectional view of the gripping structure of FIG. 15.
Figure 17:
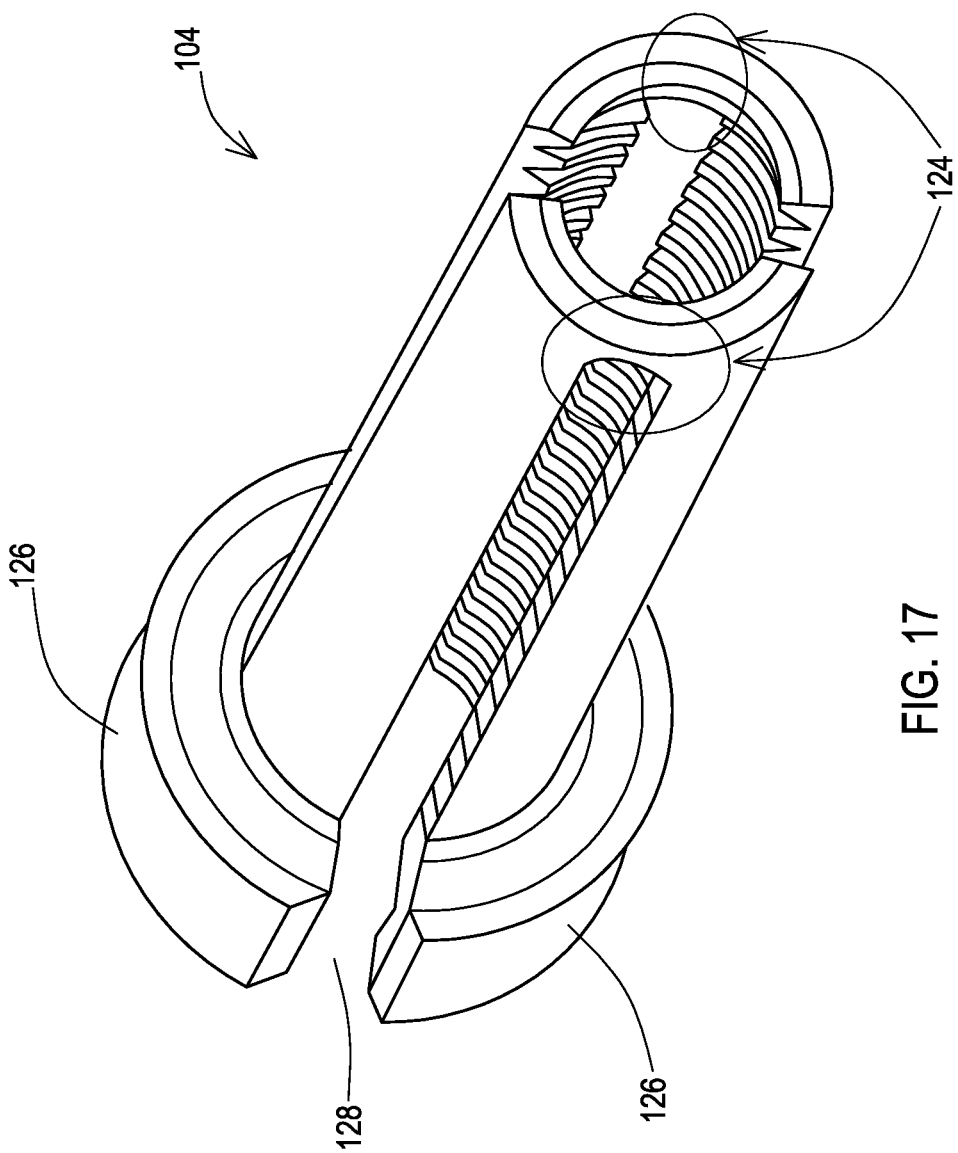
FIG. 17 is a second perspective view of the gripping structure of FIGS. 15 and 16 rotated relative to the view of FIG. 15.

FIGS. 15-17 illustrate various features of the exemplary gripping means 104. The gripping means 104 may include two zones, a shoulder zone (the zone defined by shoulder 116) and a beam zone (between 118 and 120). Beam zone 118-120 has an outer diameter of appropriate size to fit within the inner diameter of sleeve portion 106, preferably with a modicum of friction. Shoulder zone 116 and beam zone 118-120 define a lumen or passageway therethrough for accepting a stimulation lead or catheter (which is the same as lumen 114 when the gripping means 104 and body portion 102 are assembled (e.g., the body portion is overmolded onto the gripping means).

Shoulder zone 116 functions to provide an anchor point for the gripping means 104 within the body portion 102. This mechanical fixation within the body portion 102 facilitates the gripping means staying securely in place to avoid sliding in a longitudinal direction within body portion 102.

In addition to the shoulder 116, the gripping structure 104 may have a plurality of compressible axial segments 122 and a plurality of bridging segments 124. The axial segments 122 may be arranged in a generally parallel, spaced apart array along the circumference of the through hole 114, with each axial segment having first and second ends.

The shoulder 116 may include a plurality of shoulder segments 126 separated from one another in alternating fashion by a plurality of shoulder gaps 128 forming a generally annular array of shoulder segments 126 and shoulder gaps 128. The first ends of the axial segments 122 may be alternately bridged or unbridged by the shoulder segments 126 and shoulder gaps 128, with the shoulder segments 126 extending radially outward relative to the through hole 114 farther than the axial segments 122. The plurality of bridging segments 124 may be separated from one another in alternating fashion by a plurality of unbridged gaps 130 forming a generally annular array of bridging segments 124 and unbridged gaps 130, with the second ends of the axial segments 122 being alternately bridged or unbridged by the bridging segments 124 and unbridged gaps 130 such that the gripping structure 104 forms a serpentine arrangement of a continuous nature with the axial segments 122 alternately interconnected between shoulder segments 126 and bridging segments 124.

As discussed above with respect to the exemplary embodiment of FIGS. 7-12, the axial segment array may be viewed as defining a first infinite cylinder surrounding and tangent with the axial segment array, with the at least one of the shoulder segments (but preferably all of the shoulder segments 126) being substantially entirely radially outward of the first infinite cylinder. In addition, the axial segments 122 may also be viewed as defining a second infinite cylinder tangent with the axial segment array and sandwiching the axial segment array between the second infinite cylinder and the first infinite cylinder, with the bridging segments 124 being substantially enclosed between the first and second infinite cylinders.

In an alternative embodiment (not shown in the drawings), the bridging portion 124 could be omitted leaving the axial segments unconnected at the distal or second ends thereof.

The gripping structures 74 and 104 are illustrated as having a generally tubular configuration defining a passageway or lumen for receiving a lead or catheter. As used herein, "tubular" includes hollow cylindrical or other hollow structures, such as hollow structures having elliptical, polygonal or irregular cross sections, so long as a passageway or lumen is formed therein. As used herein, "circumference" is used broadly to include the equivalent property with respect to tubular structures as defined above.

The shoulders may function as a stabilizing mechanism for the gripping means. Once the gripping means is embedded within the body portion, the shoulder may provide a mechanical interference preventing the longitudinal movement of the gripping means relative to the body portion.

FIG. 16 is a cross-sectional view of an exemplary gripping means 104 showing the inner surface of axial segments 122. The inner surfaces of the axial segments may have features for increasing the fictional and mechanical gripping strength of the axial segments 122 against the lead or catheter. For example, a thread like surface 123 may be provided. This could also be other formed in a knurled or geometric bump configuration.

The gripping means 104 may be fabricated from a variety of materials such as engineering thermoplastics or metals. These may include, for example, thermoplastics such as polyurethane, polysulfone, polycarbonate or similar materials and metals such as titanium, stainless steel or other alloys suitable for implantation in the body.

Figure 18:
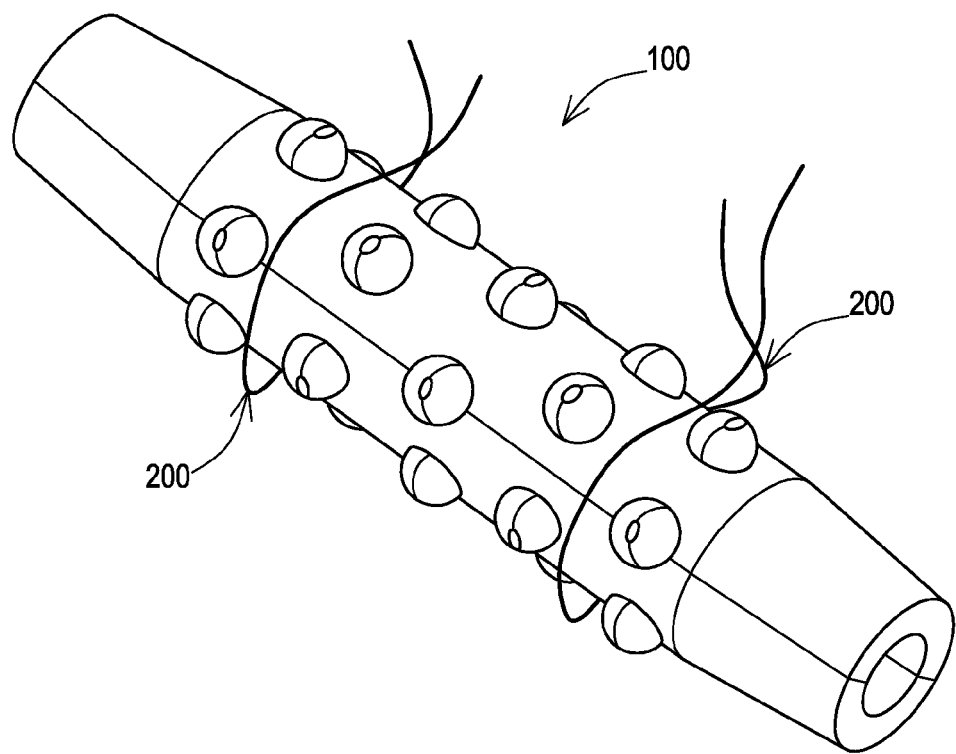
FIG. 18 is a perspective view of the medical device anchor illustrating an exemplary application of sutures.

FIG. 18 shows an exemplary application of the sutures. In use, sutures 200 may be placed around the midportion 108 of the anchor 100 and tightened sufficiently to cause a constricting force that deflects the gripping section's midportion 108. This deflection causes the axial segments 122 inner surface to engage the outer surface of the lead or catheter effecting the fixation desired. Two sutures are shown for purposes of illustration, although a single suture or more sutures may be used.

It will be appreciated that the feature of the sleeve 106 of the exemplary embodiment of FIGS. 13-18 may be combined with the double shoulder embodiment illustrated in FIGS. 7-12. In this case the sleeve (not shown) may have generally tubular shape with a length appropriate to allowing the shoulders to mate opposite ends of the sleeve. The effect of this matching may be to capture the gripping structure preventing it from being easily dislodged from sleeve.

The medical device anchor may be fabricated by a number of procedures. In an exemplary transfer molding process, a mold defining ½ of the outer surface of body portion 102 is filled with an elastomer such as silicone rubber. A force plate is used to provide a cavity where the gripping means 104 with sleeve portion 90 mated to it will be placed. Two such halves are filled. The force plates are removed and the gripping means with sleeve are inserted into one of the mold halves along with a mandrel to form lumen. The other half is assembled and the mold is then processed with heat and pressure to vulcanize the material. If sleeve portion 106 is omitted, elastomer may be forced into the recesses and voids of gripping means 104, possibly preventing proper actuation and loss of retention force.

In an exemplary insertion or injection molding procedure, the gripping means 104 and sleeve 106 are placed on a mandrel that forms the lumen and placed in a mold defining the outer surface of body portion 102. Under pressure, the material to be used for the body portion 102 is forced into the mold. The mandrel and sleeve 106 prevent the material from penetrating the gaps between the axial segments while allowing the shoulder or shoulders to be embedded in the material of the body portion 102.

In an examplary assembly process, the sleeve and gripping structure may be fabricated separately and then assembled. If employed, the optional sleeve, being a soft, elastomeric material, can be stretched or dilated to allow the gripping structure to be inserted into it. The body portion may be stretched over or on the gripping structure with the shoulder segments securely captured by the body portion, with the body portion being molded or otherwise formed of material that is softer and more compliant than the gripping structure.

Thus, embodiments of a medical device anchor and method of manufacture thereof are disclosed. The disclosed embodiments are presented for purposes of illustration and not limitation.

What is claimed is:

1. A method of manufacturing a medical device anchor, the method comprising:
   forming a gripping structure defining a through hole having a circumference, wherein axial, circumferential and radial directions are defined relative to the through hole, the gripping structure forming a continuous, serpentine arrangement having a plurality of compressible axial segments arranged in a generally parallel, spaced apart array along the circumference of the through hole, each axial segment having first and second ends; and a plurality of shoulder segments separated from one another in alternating fashion by a plurality of shoulder gaps forming a generally annular array of shoulder segments and shoulder gaps, the first ends of the axial segments being alternately bridged or unbridged by the shoulder segments and shoulder gaps, the shoulder segments extending radially outward relative to the through hole further than the axial segments; a plurality of bridging segments separated from one another in alternating fashion by a plurality of unbridged gaps forming a generally annular array of bridging portions and unbridged gaps, the second ends of the axial segments being alternately bridged or unbridged by the bridging segments and unbridged gaps such that the gripping structure forms a serpentine arrangement of a continuous nature with the axial segments alternately interconnected between shoulder segments and bridging segments; and
   stretching a body portion on the gripping structure with the shoulder segments securely captured by the body portion, the body portion being molded of material that is softer and more compliant than the gripping structure.

2. The method of claim 1 wherein the step of forming the gripping structure further includes:
   forming a grip-enhancing texture along a radially-inwardly facing surface of each axial segment, the grip-enhancing texture being formed for frictional engagement with a lead or catheter in use of the medical device anchor.

3. The method of claim 2 wherein the step of forming the grip-enhancing texture along the radially-inwardly facing surface of each axial segment further includes:
   forming threads or grooves along the radially-inwardly facing surfaces of the axial segments.

\* \* \* \* \*